(12) United States Patent
Nakagawa

(10) Patent No.: US 8,326,397 B2
(45) Date of Patent: Dec. 4, 2012

(54) MOUNTABLE UNIT FOR BIOLOGICAL SIGNAL MEASUREMENT AND BIOLOGICAL SIGNAL MEASURING METHOD

(75) Inventor: Kazuhiro Nakagawa, Saitama (JP)

(73) Assignee: Sony Corporation, Tokyo (JP)

( * ) Notice: Subject to any disclaimer, the term of this patent is extended or adjusted under 35 U.S.C. 154(b) by 301 days.

(21) Appl. No.: 12/816,709

(22) Filed: Jun. 16, 2010

(65) Prior Publication Data
US 2010/0331661 A1  Dec. 30, 2010

(30) Foreign Application Priority Data
Jun. 29, 2009  (JP) .................. P2009-153986

(51) Int. Cl.
*A61B 5/0478* (2006.01)
*A61B 5/0492* (2006.01)

(52) U.S. Cl. ........ 600/383; 600/386; 600/387; 600/391; 600/544

(58) Field of Classification Search .................. 600/383, 600/386, 387, 391, 544
See application file for complete search history.

(56) References Cited

U.S. PATENT DOCUMENTS

| 4,359,724 | A | * | 11/1982 | Zimmerman et al. | 340/575 |
|---|---|---|---|---|---|
| 4,595,013 | A | * | 6/1986 | Jones et al. | 600/383 |
| 6,032,064 | A | * | 2/2000 | Devlin et al. | 600/383 |
| 7,130,673 | B2 | * | 10/2006 | Tolvanen-Laakso et al. | 600/383 |
| 7,215,994 | B2 | * | 5/2007 | Huiku | 600/544 |
| 2005/0131288 | A1 | * | 6/2005 | Turner et al. | 600/391 |

FOREIGN PATENT DOCUMENTS
JP  2009-078139  4/2009

* cited by examiner

*Primary Examiner* — Lee S Cohen
(74) *Attorney, Agent, or Firm* — K&L Gates LLP

(57) ABSTRACT

Disclosed herein is a mountable unit for biological signal measurement, including: three electrodes; and a support body configured to support the three electrodes at positions corresponding to a positional relationship among a predetermined position on a forehead on one side of a face bounded by a midline, a temple position on the one side of the face, and a predetermined position on a zygomatic body on the one side of the face.

4 Claims, 10 Drawing Sheets

FRONT VIEW

SECTIONAL VIEW

STILL STATE

MOVED STATE

BRAIN WAVES   OCULAR POTENTIAL   MYOPOTENTIAL

BEFORE SLEEP ONSET (DROWSY)

SLEEP ONSET

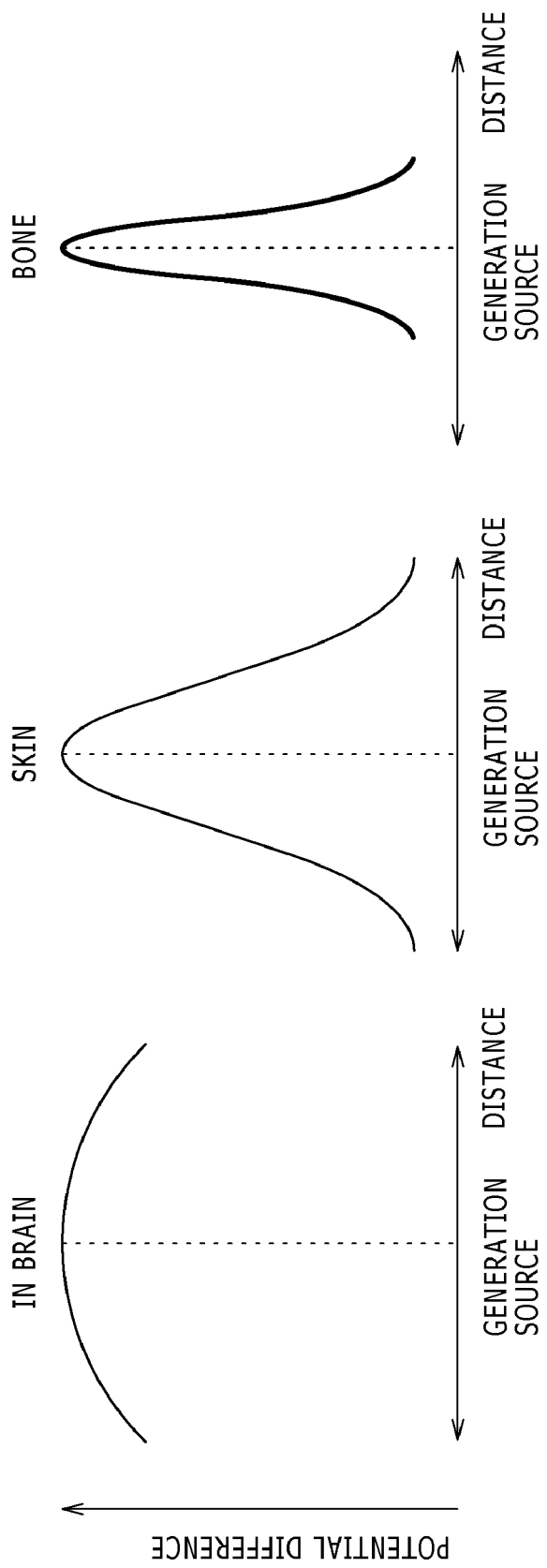

MOUNTABLE UNIT FOR BIOLOGICAL SIGNAL MEASUREMENT AND BIOLOGICAL SIGNAL MEASURING METHOD

CROSS REFERENCES TO RELATED APPLICATIONS

The present application contains subject matter related to that disclosed in Japanese Priority Patent Application JP 2009-153986 filed in the Japan Patent Office on Jun. 29, 2009, the entire content of which is hereby incorporated by reference.

BACKGROUND

The present application relates to a mountable unit for biological signal measurement and a biological signal measuring method and is suitable for e.g. a technical field to acquire waves generated and transmitted in a biological body as an electrical signal.

It is becoming apparent that the lowering of the quality or amount (time) of sleep increases the risk of various lifestyle-related diseases, e.g. circulatory diseases such as myocardial infarction and cerebral infarction, and endocrine diseases such as diabetes. Furthermore, extension of rapid eye movement (REM) sleep or the lowering of the density of the REM sleep is strongly suspected as one factor in depression. In this manner, sleep has a relation to many diseases and social problems involved by modern people, and therefore it will be more important in the future to evaluate the quality of sleep.

As a technique for sleep evaluation, a polysomnography test is known. Furthermore, there has been proposed a device for measuring the parameters necessary to evaluate the sleep cycle and the quality of sleep from the heartbeat without measuring the brain waves (refer to e.g. Japanese Patent Laid-open No. 2009-078139).

SUMMARY

However, in the polysomnography test, the period during which the test subject is tied to the testing facility such as a hospital is long, and the number of units mounted on the test subject is large. Therefore, the polysomnography test has a problem of imposing too much a burden on the test subject.

On the other hand, in the technique disclosed in the above-cited patent document, the burden on the test subject is reduced compared with the polysomnography test. However, the parameters necessary to evaluate the quality of sleep are merely indirect estimated values. Therefore, it is difficult to figure out the depth of non-REM sleep and the length and density of REM sleep, which are important to evaluate the quality of sleep, and thus this technique has a problem of inferior measurement accuracy.

There is a need for the present application to provide a mountable unit for biological signal measurement and biological signal measuring method capable of enhancing the measurement accuracy without imposing too much a burden on the test subject.

According to a first embodiment, there is provided a mountable unit for biological signal measurement, including three electrodes and a support body configured to support these three electrodes at positions corresponding to the positional relationship among a predetermined position on a forehead on one side of a face bounded by a midline, a temple position on this one side of the face, and a predetermined position on a zygomatic body on this one side of the face.

According to a second embodiment, there is provided a biological signal measuring method including the steps of (a) amplifying the potential difference between an electrode disposed at a predetermined position on a forehead on one side of a face bounded by a midline and an electrode disposed at a temple position on this one side of the face, and (b) amplifying the potential difference between an electrode disposed at a predetermined position on a zygomatic body on this one side of the face and the electrode disposed at the temple position. The biological signal measuring method further includes the step of (c) recognizing an electrooculographic waveform and an electroencephalographic waveform by using a first signal obtained as a result of amplification in the step (a) and a second signal obtained as a result of amplification in the step (b).

The temple position is a position whose distance from the boundary of the skull is short. However, it is suitable as the position of the reference electrode because the attenuation rate of the brain waves across this distance is high. The forehead position is a site that is on the skull and has no muscle thereunder. Therefore, it is suitable as the position to obtain certain measurement sensitivity to the brain waves between this position and the temple position. The position on the zygomatic body is a site close to the eye. Therefore, it is suitable as the position to obtain certain measurement sensitivity to ocular motion (ocular potential) between this position and the temple position.

The embodiments allow one electrode suitable as the reference and two electrodes that are the minimum necessary to detect the brain waves and the ocular potential to be concentrated in a local area on a one-side face bounded by the midline. Furthermore, the contact between the electrodes and the pillow can be greatly reduced even when the test subject rolls over. As a result, the degree of inhibition of sleep is greatly alleviated.

In addition, the brain waves and the ocular potential necessary for evaluation of the quality of non-REM sleep and REM sleep, which is essential in accurate determination of the sleep state, can be acquired. Thus, the measurement accuracy can be enhanced although the electrodes are concentrated in the local area.

Consequently, a mountable unit for biological signal measurement and a biological signal measuring method capable of enhancing the measurement accuracy without imposing too much a burden on the test subject can be realized.

Additional features and advantages are described herein, and will be apparent from the following Detailed Description and the figures.

BRIEF DESCRIPTION OF THE FIGURES

FIGS. 14A, 14B and 14C are graphs each showing the relationship between the human body tissue and the electrical conductivity.

DETAILED DESCRIPTION

Figure 1:
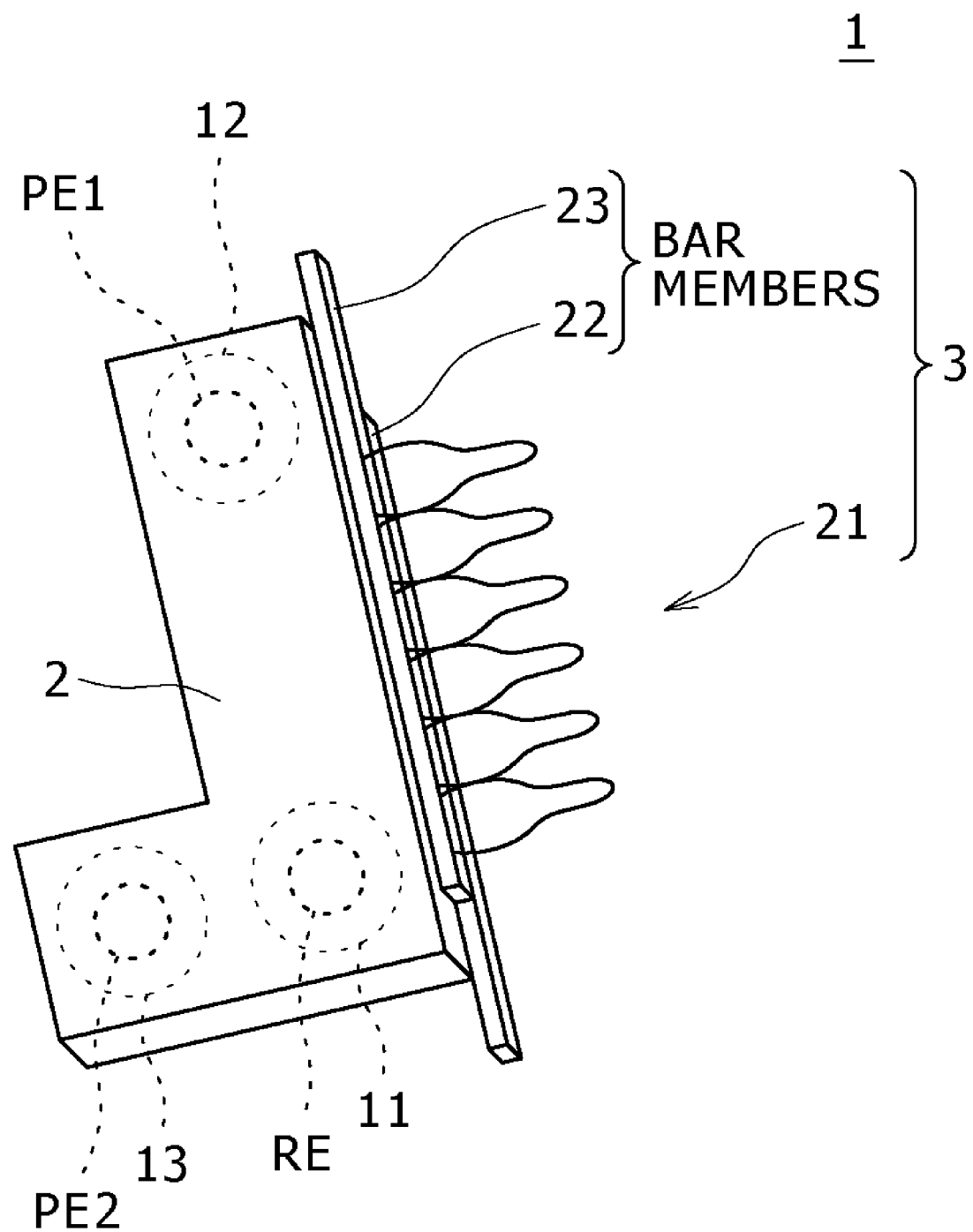
FIG. 1 is a diagram schematically showing the configuration of a mountable unit for biological signal measurement.

The present application will be described below referring to the drawings according to an embodiment.

Figure 2:
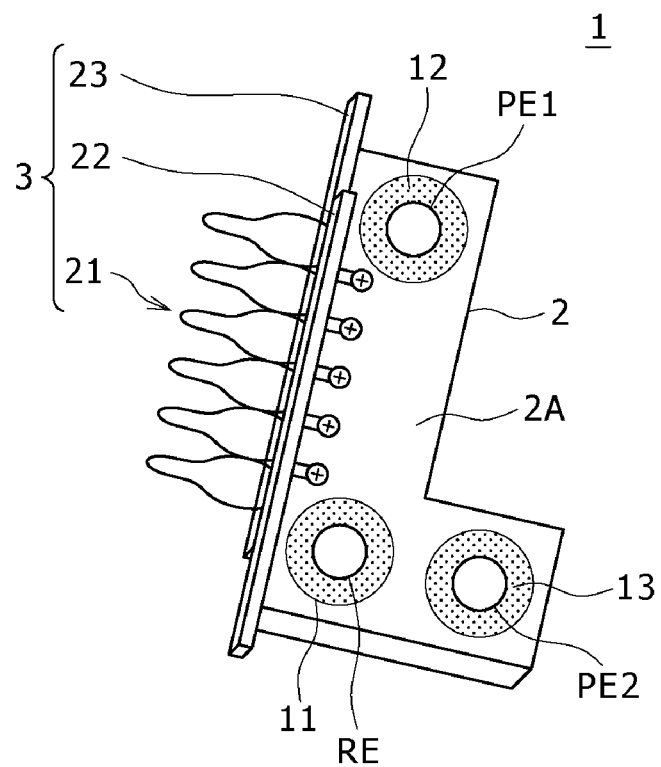
FIG. 2 is a diagram schematically showing the configuration of the mountable unit for biological signal measurement.

1. Embodiment
1-1. Configuration of Mountable Unit for Biological Signal Measurement
1-2. Mounting Procedure of Mountable Unit for Biological Signal Measurement
1-3. Configuration of Measuring Section
1-4. Advantageous Effects and So Forth
2. Other Embodiments
1. Embodiment
1-1. Configuration of Mountable Unit for Biological Signal Measurement FIG. 1 and FIG. 2 show the configuration of a mountable unit 1 for biological signal measurement. This mountable unit 1 includes a support body 2 for supporting a reference electrode RE and two probe electrodes PE1 and PE2, and a fixture 3 for fixing the support body 2 to a site on the human body as the fixing end.

The reference electrode RE is the electrode that should be disposed at a concave site on the face surrounded by the frontal bone, the zygomatic arch, and the zygomatic orbital process (hereinafter, this site will be referred to also as the temple position). The probe electrode PE1 is the electrode that should be disposed at a site on the forehead that is above the temple and on the same level as that of the frontal eminence (hereinafter, this site will be referred to also as the forehead position). The probe electrode PE2 is the electrode that should be disposed at a site on the face that is on the zygomatic body beside the tail of the eye (hereinafter, this site will be referred to also as the beside-eye position).

The support body 2 supports the reference electrode RE and the probe electrodes PE1 and PE2 at the positions corresponding to the positional relationship among the temple position on one side, the beside-eye position on the same side as this temple position, and the forehead position on the same side as this temple position.

In this embodiment, the support body 2 is formed into a plate having flexibility by using a material such as polyurethane resin, and has a structure in which one surface thereof is used as the surface that should be opposed to the human body surface and part of each of the electrodes RE, PE1, and PE2 is exposed in this surface.

Figure 3A:
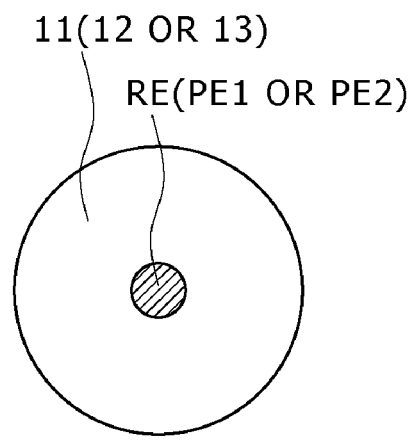
FIGS. 3A and 3B are diagrams schematically showing the configuration of a suction cup.
Figure 3B:
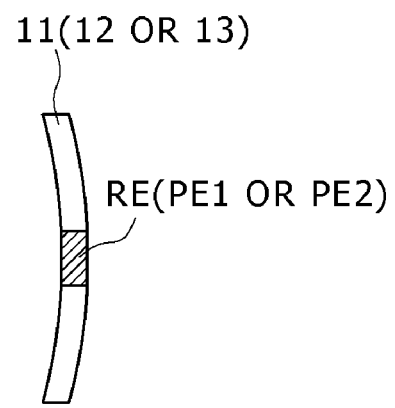

As shown in FIGS. 3A and 3B, in this support body 2, suction cups 11, 12, and 13 (see FIG. 1 and FIG. 2) each surrounding the exposed electrode part as the concave part are provided.

The fixture 3 has a part 21 composed of plural teeth aligned in one row (hereinafter, this part will be referred to also as the comb-teeth part). Each of the teeth in this comb-teeth part 21 is formed into a U-character shape by using a wire material. The roots of teeth adjacent to each other of the teeth of this comb-teeth part 21 are connected to each other. These connection parts are fixed to the support body 2 (see FIG. 2).

At positions distant from the roots of the teeth by a predetermined distance, a bar member 22 is connected to each of the parts of the teeth in this comb-teeth part 21 on one side of the U-character shape and a bar member 23 is connected to each of the parts of the teeth on the other side of the U-character shape.

Figure 4A:
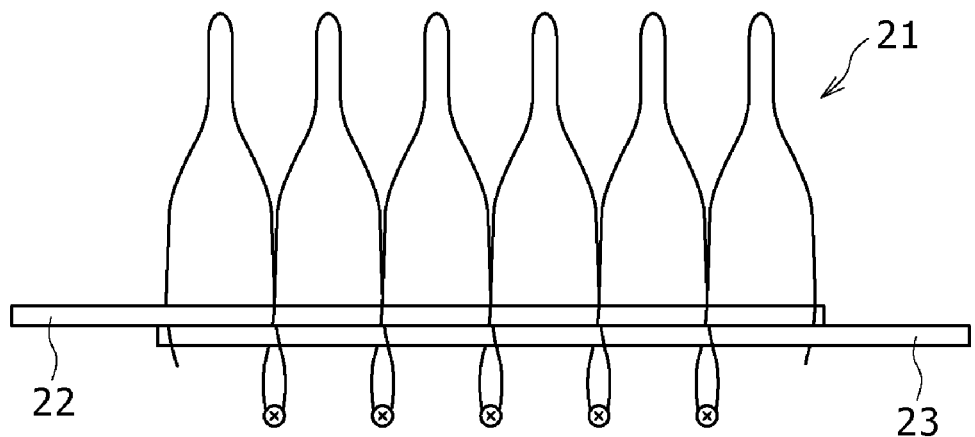
FIGS. 4A and 4B are diagrams schematically showing the configuration of a fixture.
Figure 4B:
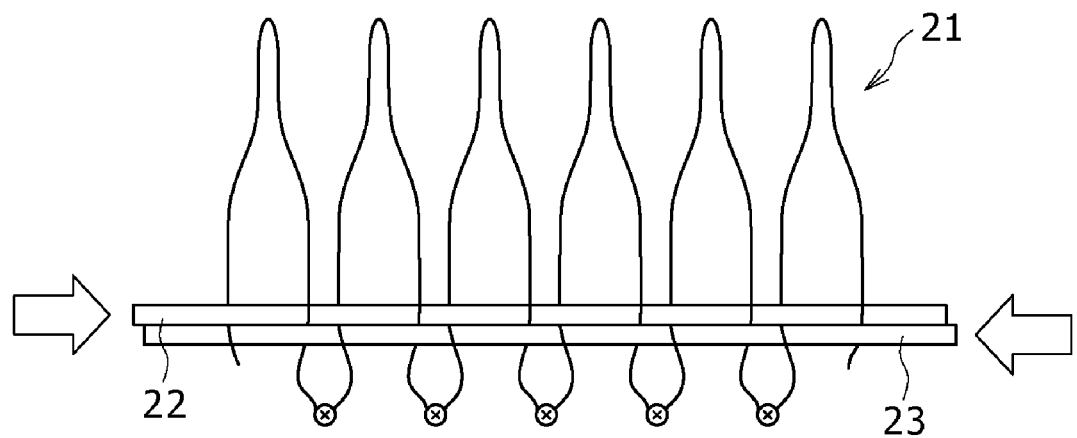

As shown in FIGS. 4A and 4B, if force is applied to these bar members 22 and 23 along such a direction that the ends of the bar members 22 and 23 are brought close to each other, the abutting parts between the respective teeth (FIG. 4A) are separated from each other by this force (FIG. 4B). Therefore, the comb-teeth part 21 is so configured as to be capable of being inserted into the head hair via the tooth tips of the respective teeth and sandwiching the head hair between the teeth.

In this manner, the fixture 3 can be attached and detached to and from the head hair, and has such a structure as to be capable of sandwiching the head hair to thereby utilize the head hair as the fixing end for the support body 2.

1-2. Mounting Procedure of Mountable Unit for Biological Signal Measurement

Figure 5:
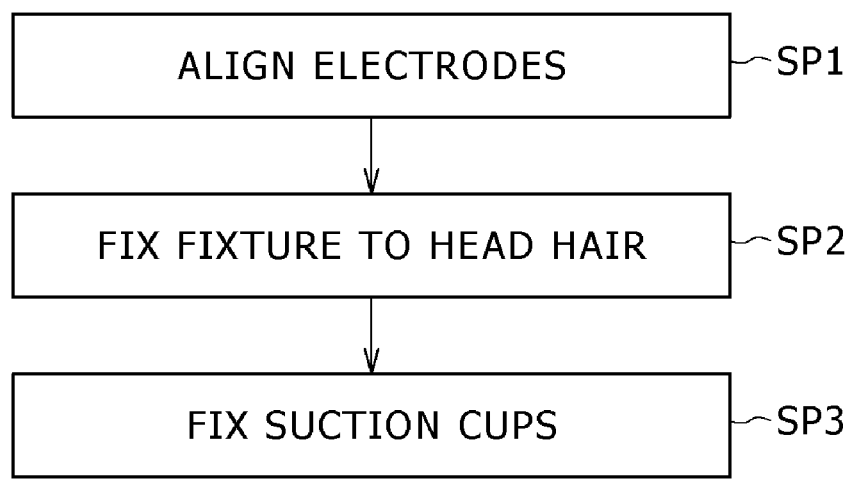
FIG. 5 is a flowchart showing the mounting procedure of the mountable unit for biological signal measurement.

FIG. 5 shows one example of the mounting procedure of the mountable unit 1 for biological signal measurement. In a first step SP1, the reference electrode RE and the probe electrodes PE1 and PE2 are aligned with the temple position, the forehead position, and the beside-eye position.

The reference electrode RE and the probe electrodes PE1 and PE2 are supported by the support body 2 at the positions corresponding to the positional relationship among the temple position, the forehead position on the same side as this temple position, and the beside-eye position on the same side as this temple position. The temple position and the beside-eye position are sites that can be easily specified without looking at a mirror or the like.

Therefore, this mountable unit 1 for biological signal measurement allows the test subject to align the electrodes by merely aligning one of the electrodes RE, PE1, and PE2 without making the test subject seek the alignment positions of the electrodes while looking at a mirror or the like.

Although the electrode position involves difference attributed to the individual variation, it has been confirmed that variation in the measurement value attributed to this difference does not cause a substantial problem in the case of the healthy adult.

In a second step SP2, the fixture 3 is fixed to the head hair. Specifically, the head hair is sandwiched between the respective linear teeth in the comb-teeth part 21. This comb-teeth part 21 has a structure obtained by aligning plural linear teeth in one row (see FIG. 1 or FIG. 2). Therefore, the fixture 3 allows the linear teeth to be smoothly inserted into the root of the head hair.

Furthermore, the comb-teeth part 21 has such a structure as to sandwich the head hair by the part from the tooth roots of linear teeth adjacent to each other to the positions in the middle of the tooth tips (see FIGS. 4A and 4B), and thus the root of the head hair can be pushed and held by the root parts of the linear teeth. Consequently, this fixture 3 can greatly reduce the movement of the support body 2 by utilizing the head hair as the fixing end.

In a third step SP3, the suction cups 11 to 13 are attached. Thereby, the reference electrode RE and the probe electrodes PE1 and PE2 are fixed at the temple position, the forehead position, and the beside-eye position in such a way that predetermined pressure is applied thereto due to the suction by the corresponding suction cups 11, 12, and 13.

Figure 6:
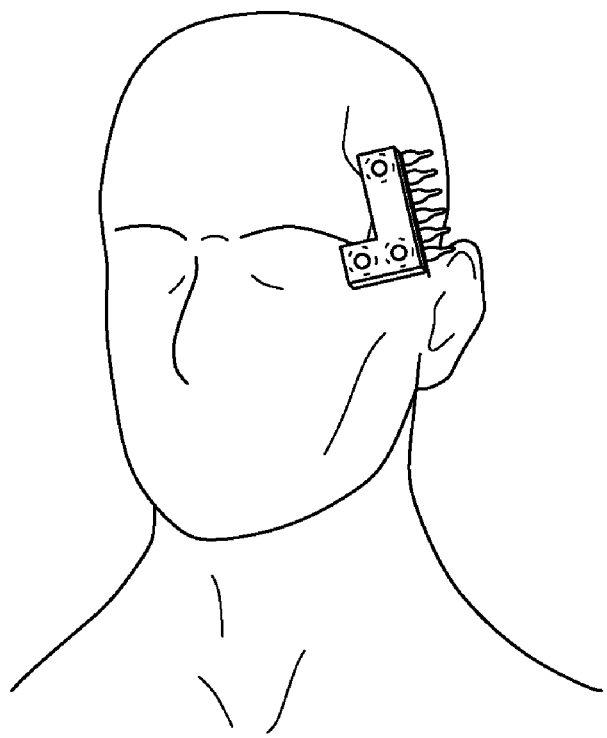
FIG. 6 is a diagram schematically showing the mounted state of the mountable unit for biological signal measurement.

Through the above-described mounting procedure, the mountable unit 1 for biological signal measurement is mounted on the human body as shown in FIG. 6 for example.

As is also apparent from FIG. 6, not only that one end of the support body 2 in this mountable unit 1 for biological signal measurement is fixed to the head hair via the fixture 3, but also that the other end thereof is fixed to the face by the suction cups 11 to 13. Thus, in this mountable unit 1, the positional movement of the electrode can be avoided to a much larger extent compared with the case in which only one side is fixed.

The temple position, the forehead position, and the beside-eye position exist in a local area of a one-side face bounded by the midline. Therefore, the support body 2 can be fixed via the suction cups 11, 12, and 13 in such a way that three electrodes RE, PE1, and PE2 concentrate in the local area on the face. Thus, this mountable unit 1 for biological signal measurement can alleviate the burden on the test subject without deteriorating the feeling of mounting for the test subject, compared with the polysomnography test, in which the number of units mounted on the test subject is large.

Furthermore, the temple position, the beside-eye position, and the forehead position are also sites that hardly get contact with the pillow even when the test subject rolls over in normal sleep. Therefore, this mountable unit 1 for biological signal measurement can greatly reduce inhibition of sleep of the test subject.

It should be noted that the above-described order of mounting is merely one example and the order of mounting is not limited thereto.

1-3. Configuration of Measuring Section

Figure 7:
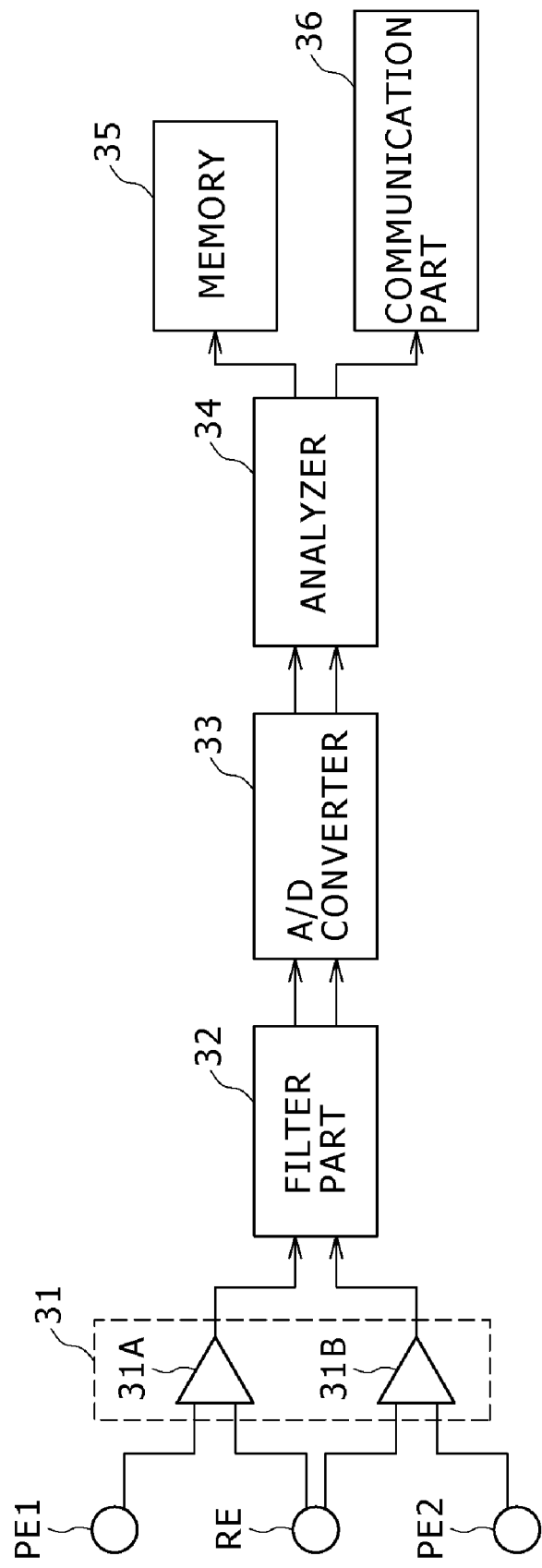
FIG. 7 is a diagram schematically showing the configuration of a measuring section.

FIG. 7 shows the configuration of a measuring section for measuring biological signals sensed by the reference electrode RE and the probe electrodes PE1 and PE2. The circuit board etc. in the measuring section is provided on the surface of the support body 2 or inside thereof for example.

This measuring section 30 includes an amplifying part 31, a filter part 32, an analog/digital (A/D) converter 33, an analyzer 34, a memory 35, and a communication part 36.

The measuring section 30 provides the supply voltage of a battery or the like to these respective parts 31 to 36 when receiving a measurement start command from an operating part provided on the surface of the support body 2 for example. In addition, the measuring section 30 blocks the provision of the supply voltage when receiving a measurement stop command from the operating part.

The amplifying part 31 has two differential amplifiers 31A and 31B. The differential amplifier 31A amplifies the potential difference between the probe electrode PE1 and the reference electrode RE as a biological signal, and outputs the amplified biological signal to the filter part 32. Because the probe electrode PE1 is disposed at the forehead position, the biological signal output from the differential amplifier 31A is a signal reflecting mainly the brain waves (hereinafter, this signal will be referred to also as the electroencephalographic signal).

The differential amplifier 31B amplifies the potential difference between the probe electrode PE2 and the reference electrode RE as a biological signal, and outputs the amplified biological signal to the filter part 32. Because the probe electrode PE2 is disposed at the beside-eye position, the biological signal output from the differential amplifier 31B is a signal reflecting mainly the ocular potential (hereinafter, this signal will be referred to also as the electrooculographic signal).

The reference electrode RE and the probe electrodes PE1 and PE2 are made to abut against the human body skin in such a way that predetermined attractive force is applied to the human body skin by the suction cups 11 to 13. Therefore, the degree of tight contact of the electrodes RE, PE1, and PE2 with the human body surface is higher compared with the case in which the electrodes are merely made to abut against the human body surface.

Furthermore, as described above, not only that one end of the support body 2 for supporting the respective electrodes RE, PE1, and PE2 is fixed to the head hair via the fixture 3, but also that the other end thereof is fixed to the face by the suction cups 11 to 13. Thus, the degree of movement of the electrodes RE, PE1, and PE2 relative to the human body surface is reduced compared with the case in which only one side of the support body 2 is fixed.

Therefore, the amplifying part 31 can accurately amplify the potential difference in a biological body. As a result, the sensitivity in the measuring section is greatly enhanced.

Furthermore, the temple position, the forehead position, and the beside-eye position are positions on bone. Therefore, the myopotential component is small in the biological signals obtained from the reference electrode RE and the probe electrodes PE1 and PE2, and the sensitivity to the brain waves and the ocular potential is greatly enhanced.

The frequency band that should be covered as the measurement subject is set for the filter part 32. The filter part 32 removes signal components other than those of the set frequency band from the electroencephalographic signal and the electrooculographic signal, and gives the electroencephalographic signal and the electrooculographic signal resulting from the removal to the A/D converter 33.

The kinds of brain waves are as follows: delta wave (1 to 3 Hz), theta wave (4 to 7 Hz), alpha wave (8 to 13 Hz), beta wave (14 to 30 Hz), gamma wave (31 to 64 Hz), omega wave (65 to 128 Hz), rho wave (129 to 512 Hz), and sigma wave (513 to 1024 Hz). Part or all of them are variably set as the frequency band that should be covered as the measurement subject by the predetermined operating part. The ocular potential is included in the frequency band corresponding to the brain waves.

The A/D converter 33 converts the electroencephalographic signal to digital data (hereinafter, this data will be referred to also as the electroencephalographic data), and gives the electroencephalographic data to the analyzer 34. Furthermore, the A/D converter 33 converts the electrooculographic signal to digital data (hereinafter, this data will be referred to also as the electrooculographic data), and gives the electrooculographic data to the analyzer 34.

The analyzer 34 includes a CPU (central processing unit), a ROM (read only memory), a RAM (random access memory) serving as the work memory of the CPU, a speaker, and a clock (timing part). In this ROM, a program for executing analysis processing, data indicating the level under which the electrode should be regarded as being not in contact with the human body surface (hereinafter, this level will be referred to also as the non-contact level threshold), and so on are stored.

When receiving a measurement start command, the analyzer 34 deploys the program stored in the ROM in the RAM, and executes processing of detecting whether or not the contact of the electrode is present (hereinafter, this processing will be referred to also as the electrode contact detection processing) and measurement processing in accordance with the program.

One example of the specific content of this electrode contact detection processing will be described below. The analyzer 34 compares the average of the level of the electroencephalographic data and the average of the level of the electrooculographic data in each prescribed period with the threshold set for the averages (hereinafter, this threshold will be referred to also as the non-contact level threshold).

If at least one of these level averages is lower than the non-contact level threshold, the analyzer 34 determines that the electrode is not in contact with the human body surface to stop the processing and notify that the electrode should be mounted again via the speaker.

In contrast, if both of the level averages are higher than the non-contact level threshold, the analyzer 34 determines that the electrode is in contact with the human body surface, and stores the electroencephalographic data and the electrooculographic data of this prescribed period in the memory 35 with association of these data with each other.

The electrode contact detection processing is executed in this manner. However, this content of processing is merely one example.

Figure 8:
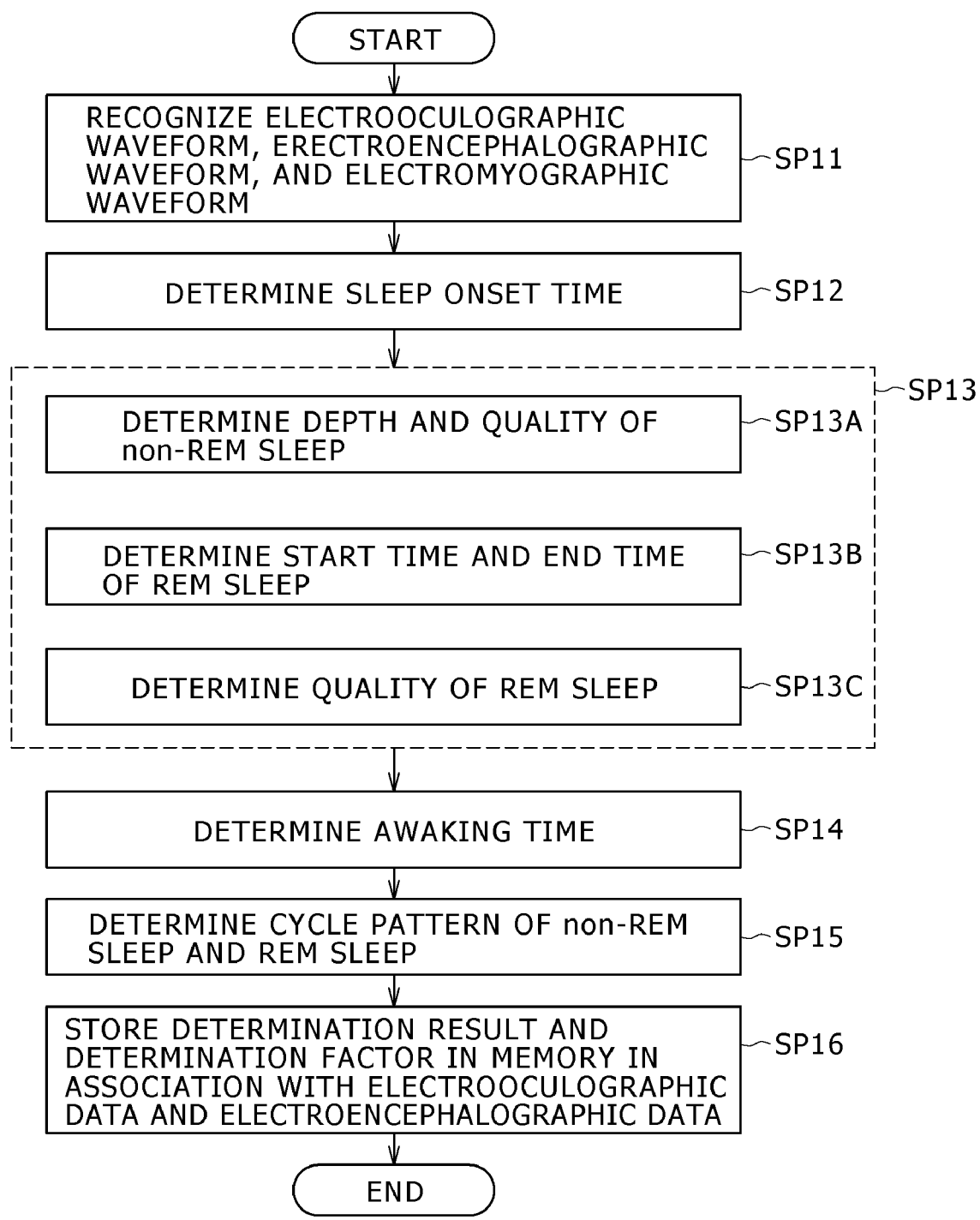
FIG. 8 is a flowchart showing the procedure of measurement processing by the measuring section.

Next, one example of the specific content of the measurement processing will be described below with use of a flowchart shown in FIG. 8. Specifically, in a first step SP11, the analyzer 34 recognizes the electroencephalographic waveform, the electrooculographic waveform, and the electromyographic waveform based on the waveform shapes in the electroencephalographic data and the electrooculographic data and the levels thereof.

In this embodiment, the electroencephalographic waveform is included in not only the electroencephalographic data but also the electrooculographic data. However, the electroencephalographic waveform appears as potential change larger than that in the electrooculographic data because the probe electrode PE1 serving as the acquirer of the electroencephalographic data is disposed at the forehead position as described above. Therefore, of the electroencephalographic data, the waveform of the potential that is lower than potential in the electrooculographic data but shows the same change as that of this potential in the electrooculographic data is recognized as the electroencephalographic waveform.

The electrooculographic waveform is also included in not only the electrooculographic data but also the electroencephalographic data. However, the electrooculographic waveform appears as potential change larger than that in the electroencephalographic data because the probe electrode PE2 serving as the acquirer of the electrooculographic data is disposed at the beside-eye position as described above. Therefore, of the electrooculographic data, the waveform of the potential that is lower than potential in the electroencephalographic data but shows the same change as that of this potential in the electroencephalographic data is recognized as the electrooculographic waveform.

On the other hand, of the electroencephalographic data and the electrooculographic data, the waveform other than the electroencephalographic waveform and the electrooculographic waveform is recognized as the electromyographic waveform.

Figure 9:
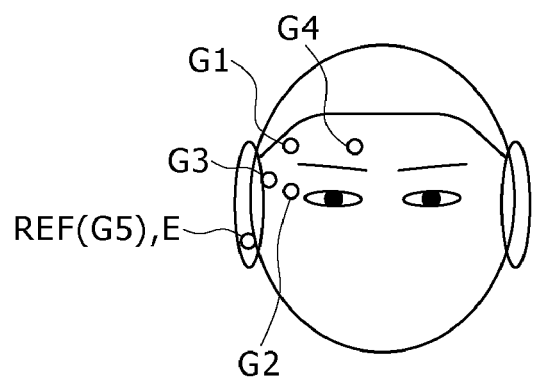
FIG. 9 is a diagram schematically showing an electrode arrangement employed in an experiment.
Figures 10A, 10B, 10C:
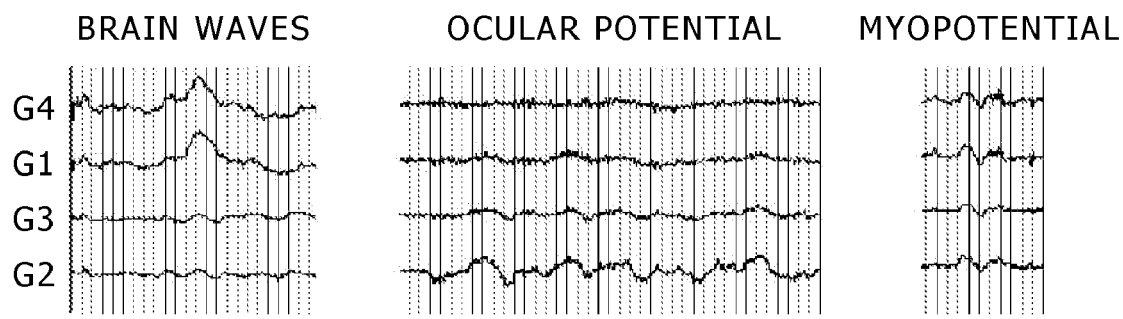
FIGS. 10A, 10B and 10C are graphs each showing the waveforms of the brain waves, the ocular potential, and the myopotential obtained by the experiment.

As an experimental result, waveforms obtained with the electrode positions shown in FIG. 9 are shown in FIGS. 10A, 10B and 10C. G1 in FIG. 9 indicates a position upwardly separated from the temple position by 4 cm (hereinafter, this position will be referred to also as the first forehead position). G2 indicates the beside-eye position. G3 indicates the temple position. G4 indicates a position laterally separated from the first forehead position by 4 cm (hereinafter, this position will be referred to also as the second forehead position). G5 indicates an earlobe position. Furthermore, G1 to G4 correspond to the probe electrodes, and G5 corresponds to the reference electrode.

As is also apparent from FIGS. 10A, 10B and 10C, the potential of the electrooculographic waveform is higher at the beside-eye position than at the other positions, and the potential of the electroencephalographic waveform is higher at the first and second forehead positions than at the other positions.

In a second step SP12, the analyzer 34 determines the time of sleep onset by using the electroencephalographic waveform and the electrooculographic waveform. Specifically, the timing at which the condition of the disappearance of the a wave and the appearance of slow eye movement (SEM) is satisfied is regarded as the time of sleep onset.

Figure 11A:
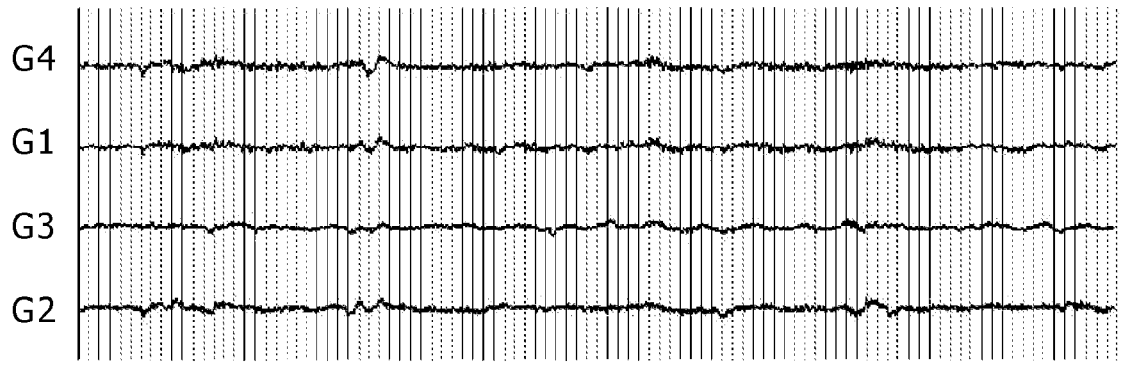
FIGS. 11A and 11B are graphs showing the electroencephalographic waveforms obtained before sleep onset and at the time of sleep onset.
Figure 11B:
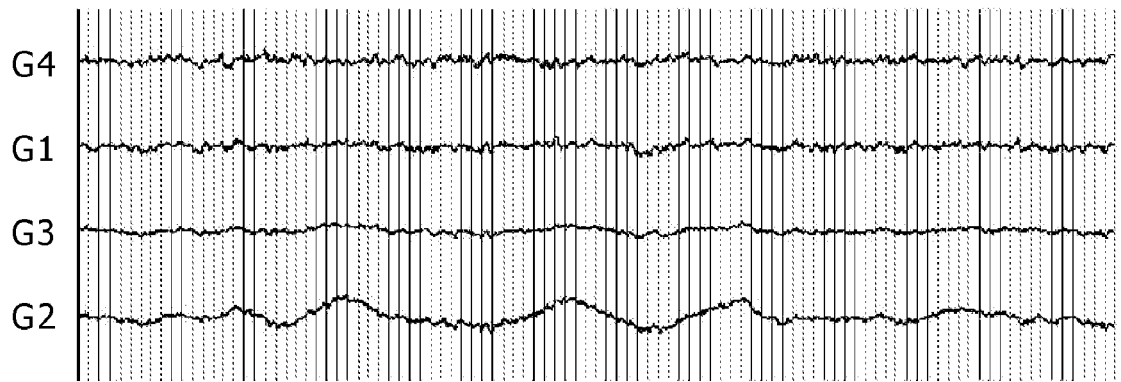

FIGS. 11A and 11B show the waveforms obtained before sleep onset and in the state of sleep onset with the electrode positions shown in FIG. 9 as an experimental result. As is also apparent from FIGS. 11A and 11B, the a wave disappears and the SEM appears upon the sleep onset.

In a third step SP13, the analyzer 34 makes various kinds of determinations relating to sleep by using the electroencephalographic waveform, the electrooculographic waveform, and the electromyographic waveform. In this embodiment, the analyzer 34 makes a determination as to the depth and quality of non-REM sleep and a determination as to the start time, end time, and quality of REM sleep.

Figure 12:
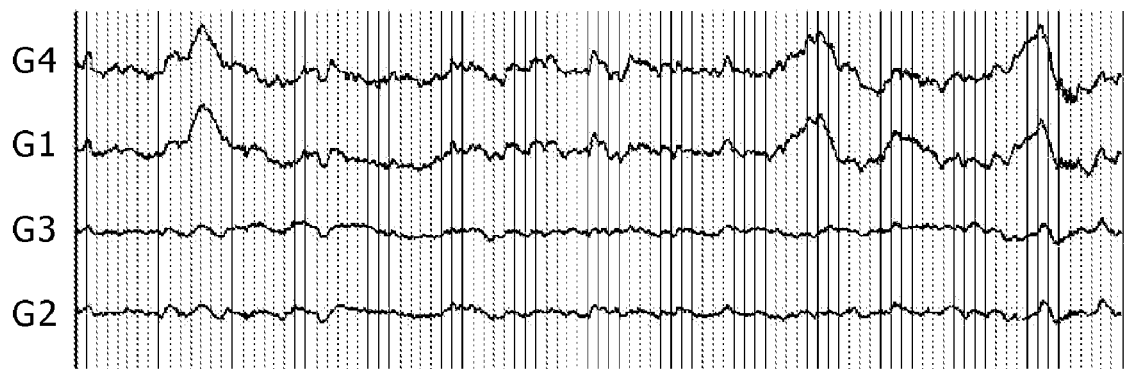
FIG. 12 is a graph showing the electroencephalographic waveform obtained at the time of non-REM sleep.

The determination as to the depth and quality of non-REM sleep is made by using the number of times of appearance of the δ wave per unit time (appearance density) and the amplitude value of the δ wave. As an experimental result, the waveform of non-REM sleep obtained with the electrode positions shown in FIG. 9 is shown in FIG. 12.

Figure 13:
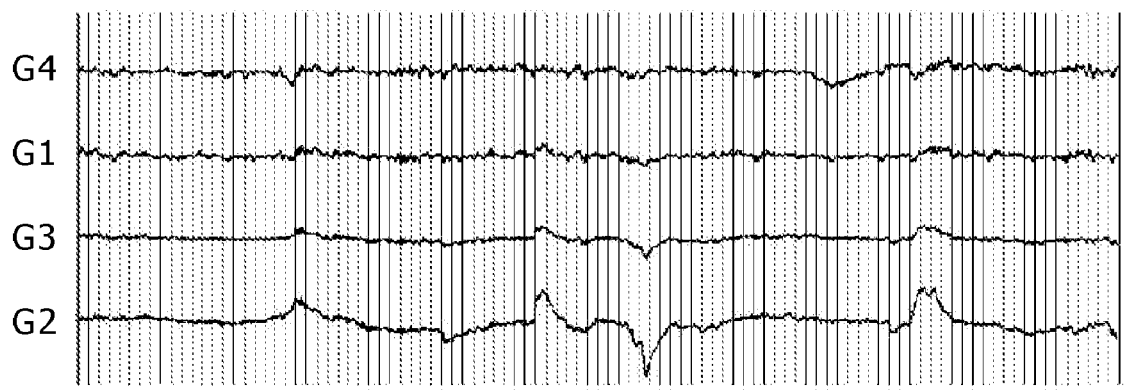
FIG. 13 is a graph showing the electroencephalographic waveform obtained at the time of REM sleep.

In the determination as to the start time of REM sleep, the timing at which the condition of the disappearance of the δ wave and the myopotential and the appearance of REM is satisfied is regarded as the start time. In the determination as to the end time of REM sleep, the timing at which the condition of the disappearance of REM and the appearance of the myopotential is satisfied is regarded as the end time. As an experimental result, the waveform of REM sleep obtained with the electrode positions shown in FIG. 9 is shown in FIG. 13.

The determination as to the quality of REM sleep is made by using the number of times of appearance of REM per unit time (appearance density) during the period from the start time to the end time of REM sleep.

In a fourth step SP14, the analyzer 34 determines the awaking time by using the electroencephalographic waveform and the electromyographic waveform. Specifically, the timing at which the condition of the appearance of the β wave and the myopotential is satisfied is regarded as the awaking time.

In a fifth step SP15, the analyzer 34 determines the cycle pattern by using the numbers of times of appearance, the ratio, the appearance cycles, etc. of non-REM sleep and REM sleep.

In a sixth step SP16, the analyzer 34 produces the determination results in the respective steps and the parameters (determination factors) used for the determinations as data (hereinafter, this data will be referred to also as the determination result data), and stores the data in the memory 35 in association with the electrooculographic data and the electroencephalographic data.

The measurement processing is executed in this manner. However, the content of processing shown in FIG. 8 is merely one example.

The memory 35 executes writing processing or readout processing in accordance with a command given from the analyzer 34 or the communication part 36. The memory 35 is not limited to a build-in memory included in the measuring section 30 but a removable memory such as a USB (universal serial bus) memory, an SD (secure digital) card memory, or a CF (CompactFlash) card memory can be used as the memory 35.

When a transmission command is given from the operating part to the communication part 36, the communication part 36 sends various kinds of data stored in the memory 35 to predetermined external apparatus by e.g. wireless transmission.

1-4. Advantageous Effects and So Forth

With the above-described configuration, in this mountable unit 1 for biological signal measurement, the support body 2 supports three electrodes RE, PE1, and PE2 at the positions corresponding to the positional relationship among the temple position, the forehead position on the same side as this temple position, and the beside-eye position on the same side as this temple position.

Therefore, this mountable unit 1 for biological signal measurement allows one electrode used as the reference and two electrodes that are the minimum necessary to detect the brain waves and the ocular potential to be concentrated in a local area on a one-side face bounded by the midline. Furthermore, the contact between the electrodes and the pillow can be greatly reduced even when the test subject rolls over. As a result, this mountable unit 1 for biological signal measurement can greatly alleviate the degree of inhibition of sleep.

In addition, in the case of this mountable unit 1 for biological signal measurement, by merely aligning one electrode with the temple position, which can be easily specified by touch without looking at a mirror or the like, the other electrodes can be aligned with the predetermined positions by the support body 2. This can greatly alleviate the burden of the mounting on the test subject.

In general, as shown in FIGS. 14A, 14B and 14C, the electrical conductivity in human body tissue greatly differs among the respective tissues attributed to difference in the water content and so on. Specifically, if the electrode is disposed on the skin on the skull, the brain waves are obtained as a signal of an equivalent level in a wide range because the distance of the transmission in the bone and the skin is short and almost constant. In contrast, at a site on the face, where the distance of the transmission in the bone and the skin is comparatively long, the signal of the brain waves extremely attenuates because of low electrical conductivity.

Therefore, the temple position, whose distance from the boundary of the skull is short, is suitable as the position of the reference electrode because the attenuation rate across this distance is high. Furthermore, the forehead position, which is a site that is on the skull and has no muscle thereunder, is suitable as the position to obtain certain measurement sensitivity to the brain waves between this position and the temple position.

The ocular potential transmits mainly through the bone and the skin. Therefore, when the probe electrode is close to the generation source, the ocular potential can be obtained as the potential difference between the electrodes even if the distance between the probe electrode and the reference electrode is short. Therefore, the beside-eye position is suitable as the position to obtain certain measurement sensitivity to ocular motion (ocular potential) between this position and the temple position.

Therefore, this mountable unit 1 for biological signal measurement can acquire the brain waves and the ocular potential necessary for evaluation of the quality of non-REM sleep and REM sleep, which is essential in accurate determination of the sleep state. Thus, the mountable unit 1 has enhanced measurement accuracy although the electrodes RE, PE1, and PE2 concentrate in a local area.

In one surface of the support body 2 of this mountable unit 1 for biological signal measurement, at least part of each of three electrodes RE, PE1, and PE2 is exposed, and the suction cups 11, 12, and 13 surrounding the exposed electrode parts as the concave parts are provided.

Therefore, this mountable unit 1 for biological signal measurement allows the electrodes RE, PE1, and PE2 to be brought into tight contact with the face surface even when a downy hair exists on the face surface or the test subject moves. As a result, without causing the positional movement of the electrode, the brain waves and so forth can be directly acquired as biological signals without the intermediary of an air layer. Thus, the measurement accuracy can be enhanced.

The support body 2 is provided with the fixture 3 for fixing the support body 2 by sandwiching the head hair. Therefore, in the case of this mountable unit 1 for biological signal measurement, not only that the electrodes RE, PE1, and PE2 are fixed by the corresponding suction cups 11, 12, and 13, but also that the whole of the support body 2 equipped with these suction cups 11 to 13 can be fixed to the head hair. Thus, this mountable unit 1 can avoid the positional movement of the electrode. As a result, the measurement accuracy can be enhanced to a larger extent.

The electrodes RE, PE1, and PE2 in this mountable unit 1 for biological signal measurement are supported by the support body 2. Therefore, this mountable unit 1 can prevent e.g. dropping of the electrode at the time of attaching or detaching to or from the face. Furthermore, the cords connected to the electrodes RE, PE1, and PE2 can be housed inside the support body 2. As a result, this mountable unit 1 can avoid the loss of the electrode at the time of attaching or detaching and entangling of the electrode in the cord. This can offer enhanced usability.

2. Other Embodiments

In the above-described embodiment, the probe electrode PE1 is employed as the electrode that should be disposed at a site on the forehead that is above the temple and on the same level as that of the frontal eminence. However, the position at which the probe electrode PE1 should be disposed is not limited to this embodiment but may be any position such as a position around area 46 of the cerebral as long as it is on the forehead.

However, in terms of enhancement in the measurement accuracy, it is more preferable that the distance between the probe electrode PE1 and the reference electrode RE be larger. Furthermore, in terms of facilitation of mounting, it is preferable that the position of the probe electrode PE1 be above the temple position or around area 46 of the cerebral.

In the above-described embodiment, the probe electrode PE2 is employed as the electrode that should be disposed at a site on the face that is on the zygomatic body beside the tail of the eye. However, the position at which the probe electrode PE2 should be disposed is not limited to this embodiment but may be any position as long as it is on the zygomatic body.

However, in terms of enhancement in the measurement accuracy, it is more preferable that the distance between the probe electrode PE2 and the reference electrode RE be larger. Furthermore, in terms of facilitation of mounting, it is preferable that the position of the probe electrode PE2 be the beside-eye position.

Although the support body 2 is an L-shape plate in the above-described embodiment, the shape of this support body is not limited to this embodiment. Any of various shapes can be employed on condition that the support body supports the electrodes at the positions corresponding to the positional relationship among the temple position on one side, the beside-eye position on the same side as this temple position, and a predetermined position on the forehead.

The support body 2 can be formed by using a single or plural various materials as long as this material is a substance that does not conduct electricity or can be regarded as a substance that does not conduct electricity (the amount of electricity conduction is smaller than the prescribed amount).

In the above-described embodiment, the fixture 3 has such a structure as to sandwich the head hair to thereby fix the support body 2. However, the structure of the fixture 3 is not limited to this embodiment. For example, a hair band can be used, or a component other than a hair band may be used.

However, in the case of using a hair band, the head is tightened by the hair band itself. Therefore, the above-described embodiment or the like is preferable in terms of the comfort of sleep. The structure of the fixture 3 is also not limited to the above-described embodiment but any of various structures can be used.

In the above-described embodiment, the suction cups 11 to 13 have such a structure as to surround the exposed parts of the respective electrodes RE, PE1, and PE2 as the concave parts. However, the structure of these suction cups 11 to 13 is not limited to this embodiment. For example, they may have a form obtained by attaching a tube to a curved electrode, like the electrode used in the electrocardiogram. It is also possible that the suction cups 11 to 13 are formed by using an adhesive material such as polyurethane.

In the above-described embodiment, the analyzer 34 for executing the electrode contact detection processing and the measurement processing is employed. However, the content of the processing by the analyzer 34 is not limited to this embodiment. For example, the analyzer 34 may execute processing of monitoring the brain waves generated from area 46 of the cerebral (the activity level of area 46) and analyzing the brain activity relating to the judgment (working memory), the reason, and the inspiration during wakefulness.

As another example, if the temple position, the beside-eye position, and the forehead position are arranged with such a positional relationship that they are at the respective vertices of a triangle and the electrical conductivity in tissue at these positions is held as data in the analyzer 34 or the like, processing of estimating the generation position of the brain waves or the myopotential can be employed.

In the above-described embodiment, the electrodes are pressed directly against the face surface. However, to these electrodes, a contact medium for efficiently transmitting waves, such as water, alcohol, oil, or glycerin, may be applied. It is also possible to employ a configuration provided with a mechanism for leading the contact medium to the electrodes.

For example, the following configuration may be employed. Specifically, a container for storing the contact medium is provided in the support body 2. Furthermore, a needle-shape tube member for leading the contact medium to the electrodes is connected to a valve provided for the container, and the tip of this tube member is disposed near one end of each electrode.

Although the measurement subject is the brain waves and the ocular potential in the above-described embodiment, the body temperature or the pulse may be added thereto. In this case, a body temperature sensor or a pulse sensor of e.g. the optical system is provided for the support body 2, and a signal given from the sensor is supplied to the analyzer 34 via the A/D converter 33. The analyzer 34 stores the body temperature data or the pulse data in the memory 35 in association with the electroencephalographic data. This association can be used as an index for specifying a sleep disorder and a disease.

The embodiments can be possibly used in the medical industry, the game industry, etc.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A mountable unit for biological signal measurement, comprising:
    three electrodes; and
    a support body configured to support the three electrodes at positions corresponding to a positional relationship among a predetermined position on a forehead on one side of a face bounded by a midline, a temple position on the one side of the face, and a predetermined position on a zygomatic body on the one side of the face, wherein
    the support body is provided with a fixture for fixing the support body by sandwiching head hair.

2. The mountable unit for biological signal measurement according to claim 1, wherein
    the predetermined position on the forehead is a position above the temple position, and the predetermined position on the zygomatic body is a position beside a tail of an eye.

3. The mountable unit for biological signal measurement according to claim 1, wherein
    the support body has a plate shape, and
    at least part of each of the three electrodes is exposed in one surface of the support body having the plate shape, and suction cups or adhesive materials surrounding the exposed electrode parts as concave parts are provided.

4. The mountable unit for biological signal measurement according to claim 1, wherein
    the support body is provided with a circuit that measures potential difference between the electrode supported at the position corresponding to the predetermined position on the forehead and the electrode supported at the position corresponding to the temple position, and potential difference between the electrode supported at the position corresponding to the predetermined position on the zygomatic body and the electrode supported at the position corresponding to the temple position.

* * * * *